United States Patent
Ahlstrand et al.

(10) Patent No.: US 6,183,458 B1
(45) Date of Patent: Feb. 6, 2001

(54) DIAPER

(75) Inventors: Ove Ahlstrand, Älvkarleby; Marlene Sandberg, Reginavägen, both of (SE)

(73) Assignee: Marlene Sandberg AB, Saltsjö Duvnäs (SE)

(*) Notice: Under 35 U.S.C. 154(b), the term of this patent shall be extended for 0 days.

(21) Appl. No.: 09/051,564

(22) PCT Filed: Oct. 21, 1996

(86) PCT No.: PCT/SE96/01342
§ 371 Date: Jun. 17, 1998
§ 102(e) Date: Jun. 17, 1998

(87) PCT Pub. No.: WO97/14385
PCT Pub. Date: Apr. 24, 1997

(30) Foreign Application Priority Data

Oct. 19, 1995 (SE) .................................................. 9503669

(51) Int. Cl.[7] .................................................. A61F 13/15
(52) U.S. Cl. .............................. 604/385.19; 604/385.01; 604/385.16; 604/395; 604/385.09
(58) Field of Search .......................... 604/385.1, 395, 604/385.19, 385.01, 385.16, 385.09; D24/126

(56) References Cited

U.S. PATENT DOCUMENTS

| | | | |
|---|---|---|---|
| 2,837,095 | * 6/1958 | Stevenson | 604/385.1 |
| 3,212,500 | * 10/1965 | Bardy | 604/385.1 |
| 3,322,122 | * 5/1967 | Daniel | 604/385.1 |
| 4,676,785 | 6/1997 | Battista . | |
| 4,968,312 | * 11/1990 | Khan | 604/388.1 |
| 5,037,413 | * 8/1991 | Haque | 604/385.1 |
| 5,062,840 | * 11/1991 | Holt et al. | 604/385.1 |
| 5,171,236 | * 12/1992 | Dreier | 604/369 |
| 5,176,672 | * 1/1993 | Bruemmer et al. | 604/385.1 |
| 5,462,541 | * 10/1995 | Bruemmer | 604/391 |
| 5,653,703 | * 8/1997 | Roe et al. | 604/385.1 |
| 5,897,544 | * 4/1999 | Ronnberg | 604/385.2 |
| 5,902,297 | * 5/1999 | Sauer | 604/385.1 |
| 5,904,674 | * 5/1999 | Bonjour | 604/385.2 |
| 6,009,558 | * 1/2000 | Rosch et al. | 2/212 |
| 6,010,490 | * 1/2000 | Freeland et al. | 604/385.1 |

FOREIGN PATENT DOCUMENTS

| | | | |
|---|---|---|---|
| 1543915 | * 4/1979 | (GB) | 604/385.1 |
| WO 95/00091 A1 | 1/1995 | (WO) . | |
| 95/07673 | 3/1995 | (WO) . | |

* cited by examiner

Primary Examiner—John G. Weiss
Assistant Examiner—Paul Shanoski
(74) Attorney, Agent, or Firm—Ware, Fressola, Van der Sluys & Adolphson LLP

(57) ABSTRACT

This invention relates to a diaper device wherein a layer (1) engaging the user is provided with an opening (15) and the layer (1) is arranged an outer layer enclosing at least one absorption body (5) wherein a layer (22) covering the absorption body has at least one opening (25) facing the user. The at least one absorption body enclosing layer (22) is part of a container (2) which is closed besides this one opening (25) connected to the opening (15) in the layer (1) engaging the user. The container has soft flexible wall portions (21) connecting its at least one absorption body enclosing outer layer with the layer (22) engaging the user and that the wall portions are so adapted that in the used position the volume of the container essentially exceeds the absorption body volume meaning that the at least one absorption body is situated at a distance from the opening or openings.

10 Claims, 4 Drawing Sheets

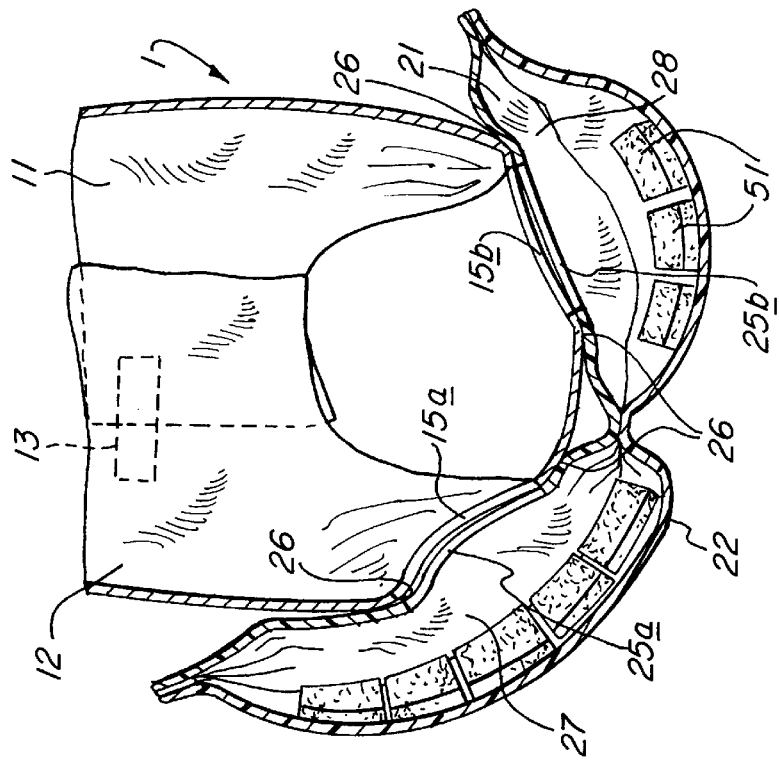
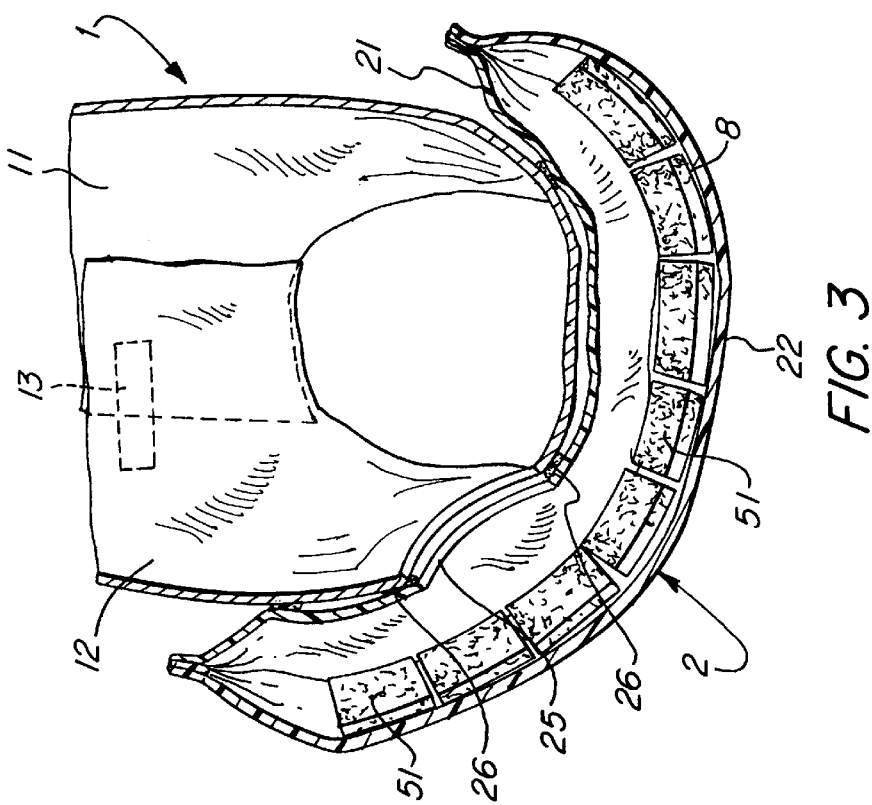

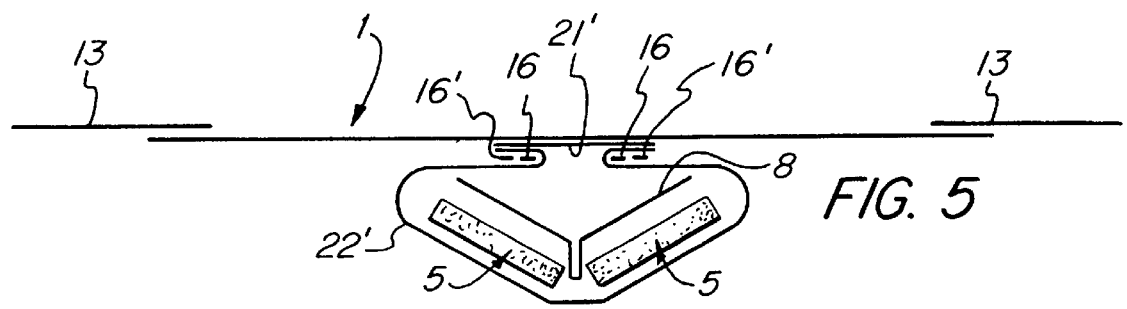
FIG. 5
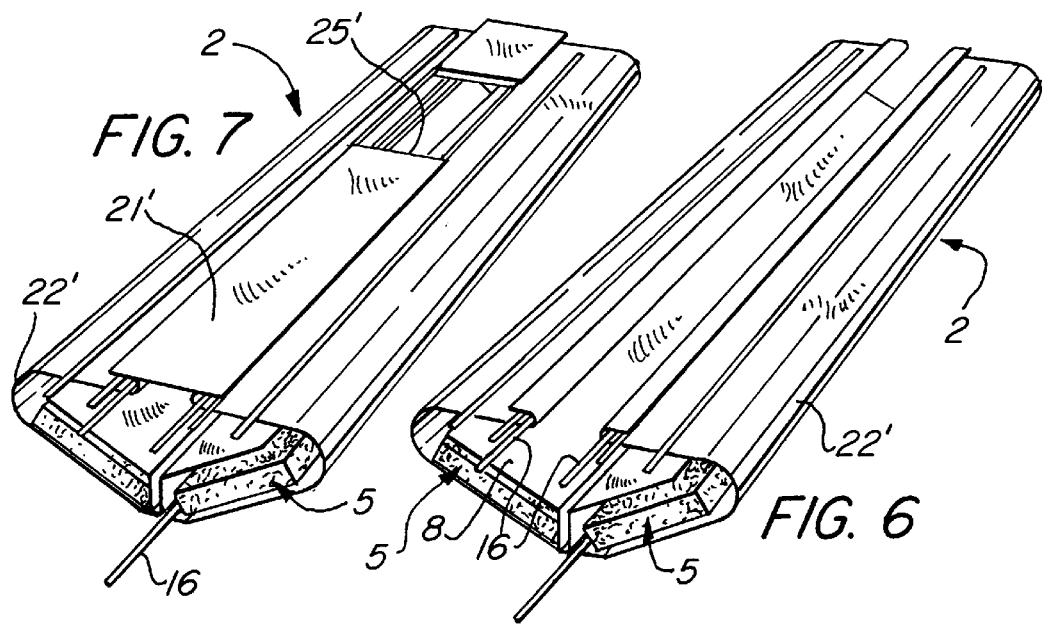
FIG. 7
FIG. 6
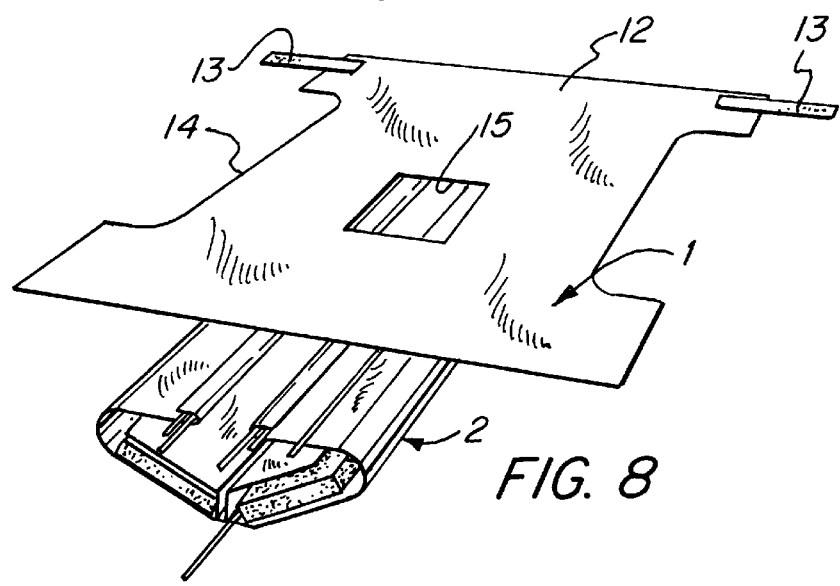
FIG. 8

DIAPER

TECHNICAL FIELD OF THE INVENTION

This invention relates to diapers those such intended for babies and such intended to be used by grown-ups with incontinence problems.

BACKGROUND OF THE INVENTION

Known all-in-one diapers include an impervious outer layer and mounted into this an absorbing material, wherein the outer layer is so arranged and shaped that it can be made to fit tightly to the body of the user and restrict the area inside from the environment. The absorbing material may be based on cellulose or be made of synthetic material.

The construction of such diapers can vary within wide limits. One intention has been to arrange the absorbing material in such a way at the impervious layer that humidity absorbed as far as possible is prevented from reaching the skin of the user beyond the place of entry and for that purpose a number of different types of pervious inner protecting layers with or without perforated or otherwise open portions. The absorbing material will then to a major part be enclosed between an outer impervious and one inner pervious layer which later has as main purpose to stabilize the absorbing material. The diaper as a whole will then after being put on form a trouser like article where a central portion by stretching or wrinkling strings attached to the material is adapted to contract so that a good fit at the crotch of the user is achieved.

With known diapers, it is so that both urine and feces especially the later will remain against the skin of the user which naturally is unwanted as, among other things, irritation of the skin easily occur. Concerning urine, it is found that even if it is absorbed by the absorbent material, the damp surface thereof will contract the skin which is undesirable.

With the majority of all diapers, the absorbing material is arranged in such a way that it in use contacts or is close to the skin of the user. This means that urine and feces will be spread or distributed in the space between the skin and absorbing layer. On urinating, it often occurs with larger volumes that urine will come outside the absorbing material and seep out at the edges of the outer layer of diaper and wet the clothing. On manufacturing of diapers and estimating of necessary volume of absorbing material, it is counted from a theoretical average volume and the ability and speed of absorption will be adapted thereto. When the volume exceeds the calculated volume, leakage is unavoidable. Generally it may be said that one disadvantage with absorption material used today is that it lacks the ability to quickly absorb anything but rather small amounts despite having a total capacity of absorption which is usually sufficient.

In known diapers, the urine will hit a generally flat surface of the absorption body which is unable to immediately absorb more than a restricted volume. Thus, the urine volume will spread over the surface of the absorption body or adjacent skin portions or impervious or surface layers, respectively, resulting in an undesired leakage.

Because of their shape and location, known absorption bodies can be easily pressed together and deformed which leads to reduced absorption ability in such portions which are compressed and also possibly leakage.

The circumstance that fluid will be absorbed over the surface only of known absorption bodies means that their absorption ability not is taken full advantage of.

Long before the modern diapers came into use there were several types of trouser like articles inside which could be placed cellulose wadding or similar absorbing material. In order to restrict the spreading of urine and feces as much as possible and position the absorbing material, U.S. Pat. No. 2,538,758 suggests such a trouser like article with buttoning at one side and provided with a partly double crotch portion where an inner layer to the major part was removed so that a pocket with excess from the upper side for a cushion like body of absorbing material was formed. Stretching tape at each side of the inwardly open pocket were intended to secure tight fitting against legs and the skin outside the crotch portion. The intention behind the known construction was that urine and feces would end up directly in the absorbing material and not soil the inside of the remaining portion of the article.

In other respects, the known device had the same disadvantages with irritating skin etc. as other diapers where urine and feces are in contact with the skin.

U.S. Pat. No. 4,662,877 discloses an example of a later embodiment of the diaper device just mentioned and is of a disposable type. In an inner layer facing the user, there is an elongated opening allowing urine and feces to directly end up at the absorbing material which is directly accessible through said opening. As in the earlier example, the surface of the absorption body will directly contact the skin of the user having the result that urine will be spread over the skin before it is absorbed and that feces remains at the skin.

One feature with all diapers, both those of today and older ones is the following. However careful and however well fitted in a diaper is, i.e. snugly contacting around the legs and the body and at the crotch, the diaper will change its shape and be displaced as soon as any mentionable amount of urine is absorbed by the absorbing material. The increase of weight caused by the urine on the absorption body outwardly restricted by the outer layer of the diaper together with the change of structure caused by the absorption of liquid as well as the stiffness of this material result in a deformation of the total diaper and also prevent the tight fitting at the user. The result of this is naturally that leakage can occur both at next urinating occasion and when the user moves and/or sits down and compresses the displaced portions of the absorption body.

PURPOSE OF THE INVENTION

One essential aspect of the invention is to bring about a diaper so arranged that it without risk for leaks is able to receive and absorb also large volumes of urine. Thus a diaper with a buffer or storage function so that even volumes exceeding the volume which the absorption material is able to manage immediately can be stored in a controlled manner during time necessary for the absorption.

Another essential aspect of the invention is to bring about a diaper which, without being deformed and losing its shape, can receive an amount of urine and/or feces and where the urine and/or feces is prevented from contacting the skin of the user.

Still another aspect of the invention is to bring about a diaper where the major part of the material engaging the skin of the user is of an air and moisture pervious type and preferable is a woven or non-woven textile material or textile similar material.

One aspect is also to bring about a diaper where the so called wet compress effect is eliminated.

Still another aspect of the invention is to bring about a diaper which as a whole may be biodegradable.

SUMMARY OF THE INVENTION

The invention includes a first or base layer the majority of which is constituted by a textile or textile like material pervious to air and humidity which layer is intended to engage the skin of the user and includes front and rear portions to be placed around the body of the user and attached to each other and an intermediate narrower portion; a closed container made of impervious foil or sheet material which is discreetly connected to the intermediate portion of the base layer adjacent its center line; at least one opening arranged so that it intersects both the wall of the container facing the intermediate portion and corresponding portion of the later. Inside the container, there is at the wall opposite to the opening arranged absorbing material which is foldable in a guided way and also when utilized for maximal absorption fills a limited part of the space inside the container.

In order to position the absorption material inside the closed container, it is covered with a tissue type material easily permeable for liquid which material is secured to the foil material forming the container in such a way that the absorption material is kept in intended position and at least one longitudinal channel is formed.

Because of the increasing weight which occurs as more and more urine is absorbed, the liquid soaked absorption material as with other diapers—especially if the user stands or walks around—has a downwards directed influence. In conventional diapers, this leads to a displacement of the whole diaper device so that it slips down and start to leak. In the diaper according to this invention, only the container will, thanks to the dimensioning of the soft material in its wall portions, be more folded out until the container walls are fully extended. As the container with absorption material, thanks to the soft flexible container walls can move relatively freely, the load will be distributed on the carrying base layer in a favorable manner and its position around the body and the legs will not be essentially influenced.

As the only connection between the container enclosing the absorption material and the face of the base layer engaging the skin is the opening or the openings in the container and the base layer, urine and feces will be kept inside the container space and thereby remote from the skin. This means that the inconvenience of having urine soaked absorption material as well as the feces engaging the skin is fully eliminated and that only the skin will be engaged by the humidity and air impervious material portion only at sides where the container material is secured to the base layer.

BRIEF DESCRIPTION OF THE DRAWINGS

Below the invention will be described with references to the annexed drawings, in which FIG. 3 is a schematically longitudinal section in a larger scale of a diaper according to FIG. 2 in position of use, FIG. 4 is a schematically longitudinal sectional view also in a larger scale of an alternative preferred embodiment of the diaper in its used portion, FIG. 5 is a schematically sectional view showing a modified embodiment, FIG. 6 is a schematically perspective view of the embodiment according to FIG. 5, FIG. 7 is a view similar to that according to FIG. 6 in a subsequent step of assembling, and FIG. 8 is a perspective view illustrating the joining of the base layer with the other parts.

DETAILED DESCRIPTION OF PREFERRED EMBODIMENT

Figure 1:
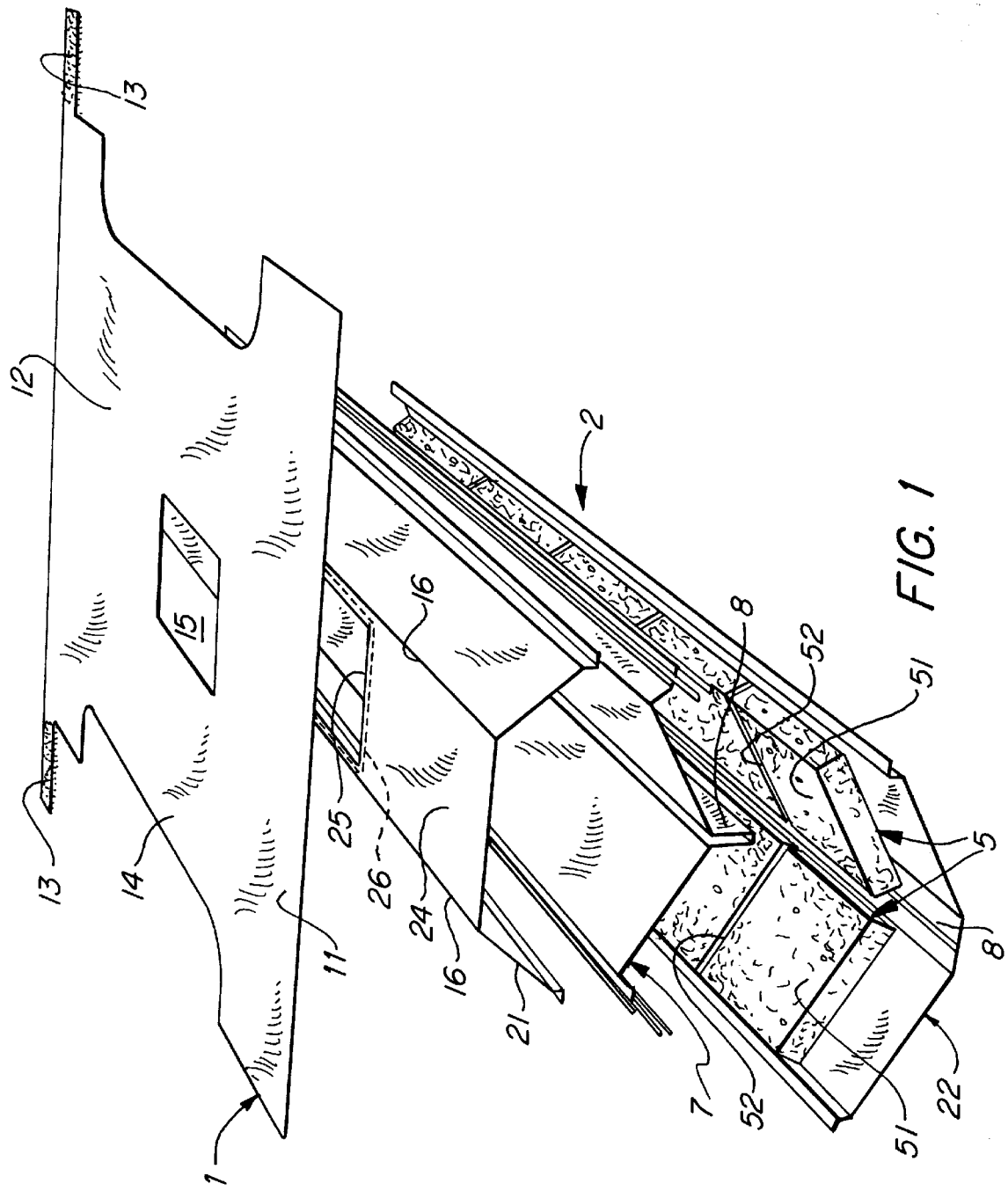
FIG. 1 is a perspective exploded view of a preferred embodiment of the parts or components included in the diaper according to the invention, FIG. 2 also is a schematically perspective view partly broken and partly assembled of the diaper according to the invention.

In the drawings for the sake of clarity the parts included in the diaper are in some cases shown separated even if they engage each other in the used position.

In FIG. 1, the layers included in the diaper are shown in the order they are found in the diaper.

At the top, there is a base layer or first layer 1 which forms a base layer of the diaper and is made of so called non-woven material or similar woven or not woven textile material with a non-sticking comfortable surface.

The base layer 1 in the preferred embodiment is pervious for humidity and air but it may be provided with a non-permeable coating.

As can be seen, the base layer 1 includes forward and rear wider portions 11 and 12 and a narrower middle portion 14 in which there is an opening 15. The rear wider portion 12 is provided with sticky tape 13 for joining the diaper around the body or waist of the user.

At this layer which is base part of the diaper there is a container as a unit designated 2. In the embodiment illustrated, it is made of a wall and top layer 21 and a bottom layer 22 which similar with the other plastic material parts are made of impermeable biodegradable plastic material.

In an alternative embodiment, the bottom layer 22 and the wall layers 21 may be made in one piece and have outwardly bent edges at which a longitudinal top layer provided with a hole is attached.

In the upwardly facing potion 24 of the container 2 there is a hole 25 corresponding to the hole 15 in the base layer 1. The base layer 1 and the container 2 are intended to be joined by gluing or otherwise securing the edges around the holes 15 and 25 as is indicated at 26 and with a dashed line in FIG. 2. The layers of the container 2 forming its bottom and the walls are in the embodiment illustrated joined along their edges and the joining may as already indicated be arranged at the top side of the container. Besides around the holes 15 and 25, the base layer 1 and the container 2 may be joined by means of discrete glue dots or the like for the purpose of stabilization.

The material layer 22 forming the container bottom and which may be somewhat stiffer than the other soft and easily bent wall and top layers, supports the absorption material as a whole designated 5. The absorption material is in the embodiment shown divided into longitudinal bodies or sections 51 and each of these may be divided by means of intersections or grooves 52. The bodies 51 may be discretely, alternatively by surface to surface engagement, be secured to the inside of the container bottom layer 22. The absorption bodies 51 are arranged and designed so that on putting on the diaper they bend in V-shape and further are bent longitudinal. This is achieved by laterally separating the absorption bodies 51 and placing them on each side of the central line of the container bottom. Above the absorption bodies 51 there is a thin woven or non-woven loose material 7 which is arranged at least in the longitudinal space 8 between the absorption bodies 51 and secured there by means of melt glue or the like towards the inside of the container bottom 22. The cover material 7 is, also along its outer edges preferably in connection with joining the upper and lower container layers 21 and 22, joined along their outer edges. The absorption bodies 51 will then be secured. The fold of double folded material pulled down between the absorption bodies 51 and secured to the container bottom 22 and also forming the longitudinal space or groove 8 as well as lateral grooves 52 between portions of the lateral bodies 51 results in an easy bending of the container bottom and the absorption material portions secured thereto not only in V-shape but also laterally. The interspace 8 and the grooves 52 besides that add to the ability of quickly absorbing liquid and humidity by increasing the absorption surface.

The layer 7 may also be folded down and secured to the container bottom 22 at the lateral spaces or grooves at 52.

Figure 2:
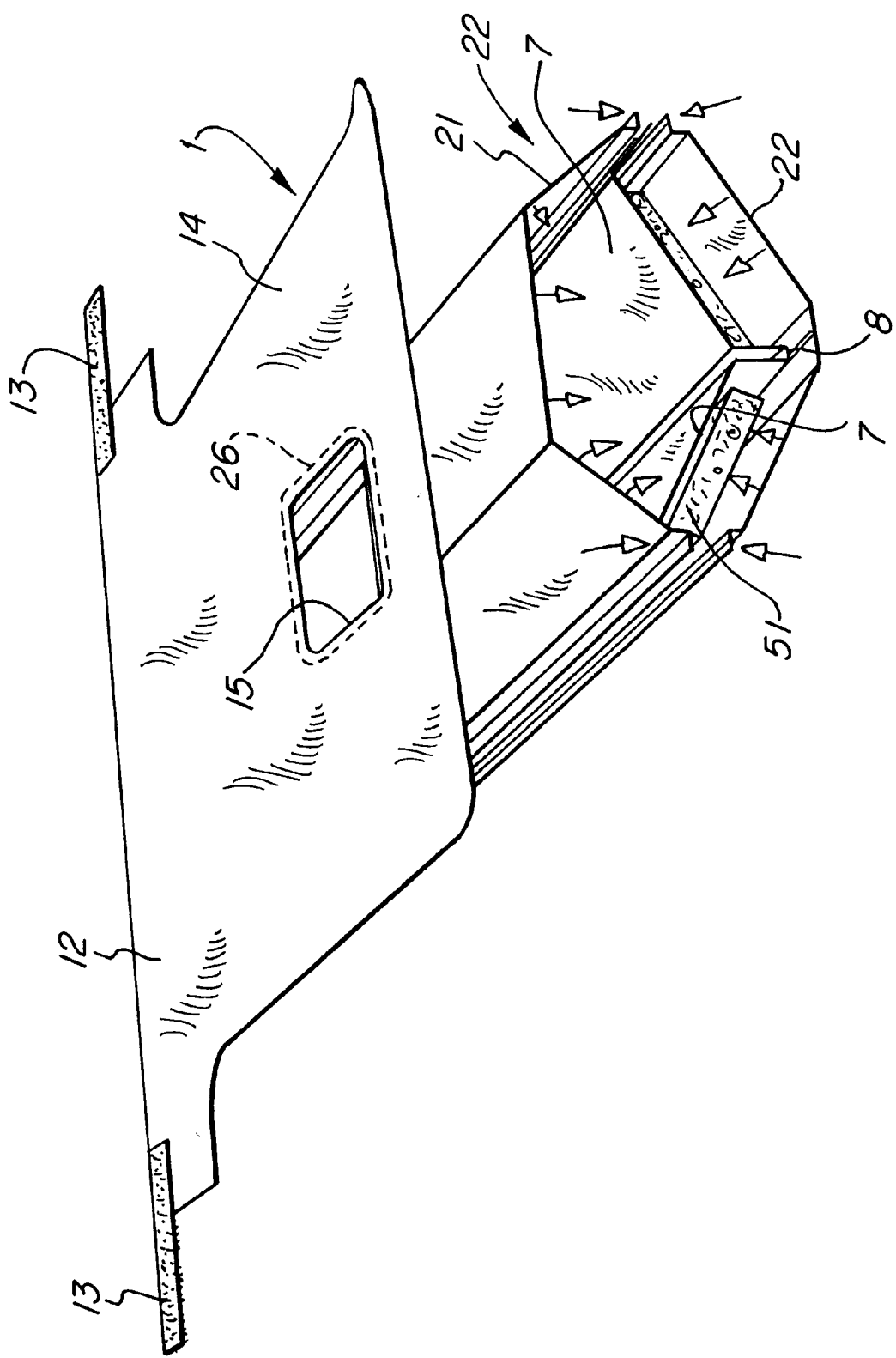

The total length of the absorption bodies 5 is so adapted that on each end the layers 21 and 22 forming the container 2 projects therebeyond, whereby the layers 21, 21 may be joined and secured to each other as the arrows in FIG. 2 indicate so that ends similar to the side joints are formed, i.e., so that there is formed around the container 2 a continuous joint. The length of the container 2 in its assembled position is adapted relatively to the length of the base layer 1 which in FIG. 2 for the sake of clarity is cut off so that the base layer 1 extends beyond the container 2.

In an alternative embodiment shown in FIG. 4, the base layer 1 as well as the upper layer 21 of the container are both provided with two holes 15a and 15b and 25a and 25b, respectively, and is the container 2 divided into a forward space 27 where the volume of absorbing material may be larger than in a rear space 28. The division may be achieved by limited welding 26 of the layers 21 and 22 forming the container.

The idea behind this is that urine is to be collected in the forward space 27 where there is larger volume of absorbing material 5 whereas feces are to be collected in the rear space 28 where because of smaller amount of free liquid the volume of absorbing material 5 may be reduced relatively to that of the forward space 27.

In alternative embodiments, the base layer 1 and the layer 21 forming the upper portion of the container—as well as in the embodiment with one hole—may be joined as with 26 only in the sections adjacent to the holes aligned with each other. It is also possible to use a continuous joining over an area including both the forward and the rear sets of holes.

The embodiment according to FIGS. 5–8 differs from the earlier described ones in that the container 2 primarily because of manufacturing reasons is made of a portion of the material portion 22' which thus forms bottom section, side walls and part of the top side. The edges of the layer 22' is folded over so that at each side there is formed a channel wherein rubber bands 16 may be inserted and after that the edge is glued to the layer 22' in order to form an edge stiffening which thanks to the influence of the rubber band arches to bend the upper side of the container upwardly. The upper portion of the container is glued towards double edges and the upper portion is in this case a relatively narrow strip 21' of material intersected or provided with hole 25' at the positions where the container openings are expected to be.

FIG. 5 illustrates schematically all parts of the diaper device seen in correct position but somewhat separated. In FIG. 6 is shown how the enclosing bottom and side part 22', the absorption body 5 is arranged and how the positioning thin humidity permeable layer 8 folded down between the same in order to be fasten by means of a string of glue. The free edges of the layer 22' are shown folded over with a rubber band 16 inserted into the fold and a string of glue 16 at the outer portion thereof.

FIG. 7 shows how the container 2 is closed by means of a strip shaped upper part 21' by means of glue or in any other way secured to the folded over edges over the layer 22' and the layer 21' cut off or provided with cut out holes forming the intended openings 25'.

In FIG. 8 the base layer 1 which may be identical with the base layer according to earlier described embodiments and is provided with an opening 15 the edge of which is intended to be secured around the opening 25 of the container part 2.

Also in this embodiment the ends of the container 2 are closed by joining the portions of the material 22' forming the container 2 beyond the end of the absorbing material 5 by means of compressing and gluing. The container 2 extending in each direction from the fastening points at the opening alternatively the openings may in stabilizing purpose be connected with the base layer by means of discrete dots of glue.

In the embodiments described, the upper portion of the container 2 forms a soft flexible connection between the base layer 1 applied towards the user and the container 2 in which the absorption material 5 is essentially non displaceable arranged and also adds to keep the shape of the container 2.

The soft flexible connection implies that the absorption material 5 inside the container 2 may be made to fold itself out in a controlled way or shape itself in an intended way ensuring good absorption and securing a distance relatively to the user and likewise that the absorption material 5—also when it is saturated with liquid and consequently has a considerable weight—in no mentionable extent can influence the base layer 1 so that this one in an unwanted way is displaced relatively to the user with accompanying risk for leaking. As the position of the base layer 1 in no way is influenced by the contents of the container 2, the position for the hole or the holes 15, 25, 15a, 15b and 25a, 25b, 25' is ensured which means that the risk for urine and feces to end up against the base layer instead of passing through the holes into the container 2 is eliminated.

The base layer 1 and soft flexible upper portion 21 of the container 2 also allows the diaper on packing to be pressed together to a height essentially corresponding to the thickness of the absorption bodies only.

On securing to the user, the diaper is bent around the crotch portion so that the longitudinal absorption bodies 51 formed by one or several parts, by the lateral compression of the container 2, arrange themselves in V-shape formation initially creating a free reception space for urine between the two mutually obliquely arranged bodies. By influence of the absorption bodies 51 which as they absorb more and more urine will be heavier and not yet absorb free urine the container will be weighted down under folding out of the soft flexible container layer 21 (alternatively, edge portions of layer 22') which also results in an increase of the internal volume of the container 2. As both urine and feces can pass directly into the container where absorption of free liquid and humidity takes place there will be no wetting or moistening of the base layer 1.

In order to facilitate the positioning of the diaper, rubber bands 16 or similar elastic bands may be attached primarily adjacent to the openings and preferably discretely or intermittently which acts as wrinkling band in order to pull together material in directions desired. Rubber bands arranged around the opening or the openings of the container will also stabilize the edge of these. The rubber bands 16 may at least, at the end portion of the base layer 1 provided with sticky tape pieces be attached at or adjacent this tape so that they urge to bend said end portion both longitudinally and laterally.

Unlike the majority of today's all-within-one diapers, the diaper according to this invention as a whole or a majority part thereof be made of compostable or biodegradable material. This includes also the plastic material forming the second and third layers of the container which may be manufactured on a vegetable base liquid impermeable plastic material.

What is claimed is:

1. Diaper device for use on a body of a user comprising:
   (a) a base layer to be arranged engaging the body of the user and at least partly being permeable to air and humidity, a portion of the base layer adapted to be located towards a crotch area of the user and having at least one opening;
   (b) a container provided on the base layer, the container including:
      (i) an inner layer of a soft flexible material with at least one opening corresponding in size and position to the at least one opening of the base layer, the container being closed but for at the at least one opening in the inner layer, the inner layer being tightly secured to the base layer around the at least one openings in the base layer and the inner layer, and
      (ii) a bottom portion adjoining side and top portions of the inner layer, the bottom portion being impermeable to liquid and humidity, the bottom portion being connected to the base layer and dimensioned so the bottom portion is adapted to move away from the base layer and the at least one opening therein by gradual folding out of the container, and
   (c) at least one absorption body covered by the inner layer and the bottom portion, the at least one absorption body being covered by the inner layer in a direction towards the user with the at least one openings of the base layer and the inner layer forming a passage in a direction towards the at least one absorption body,
whereby the container creates a volume due to dimensioning of the inner layer and the bottom portion considerably larger than a volume created by the at least one absorption body arranged therein after maximum absorption thereby.

2. Diaper device according to claim 1, wherein the container is an elongated shape and the at least one absorption body is made of at least two longitudinal main parts so arranged in the container that, on fitting the diaper device on the user, the parts take a mutually oblique position maintaining a groove therebetween.

3. Diaper device according to claim 2, wherein the at least one absorption body formed by the at least two parts is shorter than the container.

4. Diaper device according to claim 1, wherein the at least one opening in the base layer is two openings and the at least one opening in the inner layer is two openings communicating with the two openings in the base layer, the base layer and the inner layer around the openings of the base layer and the inner layer are joined to each other.

5. Diaper device according to claim 4, wherein the container in a longitudinal direction is divided into two spaces wherein one opening of the inner layer communicating with one corresponding opening of the base layer is arranged at each space and the at least one absorption body is absorption bodies arranged in each space.

6. Diaper device according to claim 5, wherein the absorption bodies are made of absorbing material and a larger volume of absorbing material is arranged in one of the spaces than in the other space.

7. Diaper device according to claim 1, wherein, besides having the inner layer and the base layer joined around the at least one openings of the base layer and the inner layer, the container is discreetly connected to the base layer, for the purpose of stabilization.

8. Diaper device according to claim 1, wherein the at least one absorption body is longitudinal rows of absorption bodies separated by lateral spaces and arranged at each side of a longitudinal space, the absorption bodies are positioned relatively to a lower part of the container by means of a stabilizing layer stretched into at least the longitudinal space between the longitudinal rows of the absorption bodies and connected to the bottom portion.

9. Diaper device according to claim 8, wherein the base layer, the absorption bodies and the stabilizing layer are made of compostable, degradable material and the inner layer and bottom portion forming the container are made of compostable, degradable plastic material.

10. Diaper device according to claim 1, wherein the base layer and the at least one absorption body are made of compostable, degradable material and the inner layer and bottom portion forming the container are made of compostable, degradable plastic material.

* * * * *

UNITED STATES PATENT AND TRADEMARK OFFICE
CERTIFICATE OF CORRECTION

PATENT NO. : 6,183,458 B1  
DATED : February 6, 2001  
INVENTOR(S) : Ove Ahlstrand and Marlene Sandberg Page 1 of 1

It is certified that error appears in the above-identified patent and that said Letters Patent is hereby corrected as shown below:

Title page,
Under FOREIGN PATENT DOCUMENTS, add,
-- 502 549 C2    9/1995    (SE) --.

Title,
Should be -- Diaper Device For Use On A Body of A User --.

Column 3,
Line 32, after "more", -- and more -- should be inserted.
Line 34, after "walls", -- , --, should be inserted.

Column 5,
Line 16, "21,21", should be -- 21,22 --.

Column 6,
Line 45, "," should be deleted.

Signed and Sealed this

Twentieth Day of November, 2001

Attest:

NICHOLAS P. GODICI  
*Attesting Officer*   *Acting Director of the United States Patent and Trademark Office*